United States Patent [19]

Mascuch et al.

[11] Patent Number: 4,763,665
[45] Date of Patent: Aug. 16, 1988

[54] SHIELDED THERMISTOR FOR MICROWAVE ENVIRONMENT

[75] Inventors: Frank Mascuch, Watchung; Arthur Winter, Short Hills; Satish Laroia, Edison, all of N.J.

[73] Assignee: Victory Engineering Company, Springfield, N.J.

[21] Appl. No.: 63,093

[22] Filed: Jun. 17, 1987

[51] Int. Cl.⁴ ............................................. A61B 5/00
[52] U.S. Cl. ................................... 128/736; 374/175
[58] Field of Search ............... 128/736, 804; 374/163, 374/175, 183, 185

[56] References Cited

U.S. PATENT DOCUMENTS

| | | | |
|---|---|---|---|
| 4,449,035 | 5/1984 | Schwob | 374/185 X |
| 4,626,110 | 12/1986 | Wickersheim et al. | 128/736 X |
| 4,627,744 | 12/1986 | Brixy et al. | 374/175 |
| 4,643,186 | 2/1987 | Rosen et al. | 128/804 X |
| 4,658,836 | 4/1987 | Turner | 128/736 X |
| 4,669,475 | 6/1987 | Turner | 128/736 X |

FOREIGN PATENT DOCUMENTS 0019815 7/1956 Fed. Rep. of Germany ...... 128/736

*Primary Examiner*—William E. Kamm
*Assistant Examiner*—Angela D. Sykes
*Attorney, Agent, or Firm*—Thomas R. Morrison

[57] ABSTRACT

A thermistor assembly for use in an environment of microwave radiation employs an interface metallic layer on the surface of a plastic insulation its conductors and a metal foil wrapped upon the thermistor head. The metal foil overlaps the interface metallic layer on the conductors. A surface metallic layer is electroplated on both the interface metallic layer and the metal foil to unite both into a single electrically conducting layer effective to exclude microwave radiation from the interior thereof and thus to avoid direct microwave heating of the thermistor or the electrical conductors in the vicinity of the thermistor.

7 Claims, 1 Drawing Sheet

SHIELDED THERMISTOR FOR MICROWAVE ENVIRONMENT

BACKGROUND OF THE INVENTION

The present invention relates to temperature sensors and, more particularly, to temperature sensors adapted for use in an environment containing microwave radiation.

U.S. patent application Ser. No. 779,285, now U.S. Pat. No. 4,681,122 the teaching of which is incorporated herein by reference, discloses apparatus for microwave thermotherapy useful in the treatment of cancerous tissue, particularly in the brain. The disclosed apparatus includes a catheter having at least two lumens extending along a substantial length thereof. The catheter is inserted into the tissue to be treated to position a microwave antenna in one of the lumens within, or very close to, the cancerous tissue. The microwave antenna is fed microwave energy of sufficient intensity and for sufficient time to damage the cancerous tissue without damaging surrounding healthy tissue.

Effective treatment requires that the cancerous tissue in the vicinity of the catheter be held at a temperature within about half a degree of 43 degrees C. for a period lasting on the order of an hour. A temperature substantially below this range is tolerated by the cancerous tissue without significant damage, and thus the treatment fails. A temperature substantially above this range can cause unnecessary damage to healthy tissue without significant improvement in the treatment result. Such fine temperature control is complicated by the fact that the amount of microwave radiation required to maintain the desired temperature decreases over a treatment period due to a reduction in the ability of heat-damaged cancerous tissue to maintain fluid circulation.

As a consequence of the preceding, the above-referenced patent application employs a thermistor in the second lumen of the catheter positioned to measure the temperature of the tissue being heated by the microwave energy. This requires that the thermistor and its leads be within the influence of microwave energy radiated by the microwave antenna. It has been discovered that the microwave energy tends to heat the thermistor chip and its leads, whereby higher temperatures are measured than would actually be measured if the only source of heat was the tissue being treated. Unless dealt with in some manner, such false temperature readings may lead to the maintenance of tissue temperatures outside the range permissible for effective treatment.

One method of dealing with microwave heating of the thermistor and its leads includes estimating the component of temperature measurement produced by the microwave energy impinging on the thermistor and its leads. This is possible in the apparatus of the referenced patent application since the geometry in the catheter is fixed and the amplitude of the microwave signal is known. Based on empirical measurements, the measured temperatures may be calibrated to yield close approximations of the actual tissue temperatures. A further method includes periodically turning off the microwave radiation to permit the temperature of the thermistor chip and its leads to reach an equilibrium temperature due solely to the tissue temperature. This technique has the drawback that tissue cooling inevitably takes place during the off period, and the rate of cooling may not be known precisely. As a consequence, the temperature measured near the end of the off period is lower than the tissue temperature during microwave radiation.

A need thus exists for a technique permitting temperature measurement simultaneously with microwave heating of tissue without the measured temperature containing substantial errors due to microwave heating of the temperature sensor.

OBJECTS AND SUMMARY OF THE INVENTION

Accordingly, it is an object of the invention to provide a thermistor assembly which overcomes the drawbacks of the prior art.

It is a further object of the invention to provide a thermistor assembly wherein a thermistor and its leads are shielded against microwave energy.

It is a still further object of the invention to provide a thermistor assembly wherein an electrically continuous metallic coating is disposed on a thermistor chip and upon insulation on electrical leads.

Briefly stated, the present invention provides a thermistor assembly for use in an environment of microwave radiation. An interface metallic layer is sputtered onto the surface of a plastic insulation covering its conductors and a metal foil is wrapped upon the thermistor head. The metal foil overlaps the interface metallic layer on the conductors. A surface metallic layer is electroplated on both the interface metallic layer and the metal foil to unite both into a single electrically conducting layer effective to exclude microwave radiation from the interior thereof and thus to avoid direct microwave heating of the thermistor or the electrical conductors in the vicinity of the thermistor.

According to an embodiment of the invention, there is provided a thermistor assembly comprising: a thermistor, the thermistor including a first insulating coating thereon, electrical conductors connected to the thermistor, a second insulating coating on the electrical conductors, the first and second insulating coating forming a continuous insulation, an interface metallic layer on the second insulating layer, an electrically conductive foil wrapped upon the thermistor and in overlapping electrical contact with a portion of the interface metallic layer, and a surface metallic layer on the interface metallic layer and the electrically conductive foil.

According to a feature of the invention, there is provided a thermistor assembly comprising: a thermistor, the thermistor including a varnish coating thereon, electrical conductors connected to the thermistor, a plastic layer on the electrical conductors, the varnish coating and the plastic layer forming a continuous insulation, an interface metallic layer of copper on the plastic layer, an aluminum foil wrapped upon the thermistor and in overlapping electrical contact with a portion of the interface metallic layer, and a surface metallic layer of gold electrically plated on the interface metallic layer and the aluminum foil.

According to a further feature of the invention, there is provided a method for forming a shielding layer on a thermistor assembly comprising: forming a first insulating coating on a thermistor, forming a second insulating coating on electrical conductors connected to the thermistor, the first and second insulating coating forming a continuous insulation, sputtering an interface metallic layer on the second insulating layer, wrapping an electrically conductive foil upon the thermistor and in overlapping electrical contact with a portion of the interface metallic layer, and electroplating a surface metallic layer on the interface metallic layer and the electrically conductive foil.

The above, and other objects, features and advantages of the present invention will become apparent from the following description read in conjunction with the accompanying drawings, in which like reference numerals designate the same elements.

BRIEF DESCRIPTION OF THE DRAWINGS

FIG. 2 is a side view of a shielded thermistor assembly of FIG. 1 removed from the remainder of the catheter to illustrate details thereof.

FIG. 3 is a cross section taken along III—III in FIG. 2.

FIG. 4 is a cross section taken along IV—IV in FIG. 2.

DETAILED DESCRIPTION OF THE PREFERRED EMBODIMENT

Figure 1:
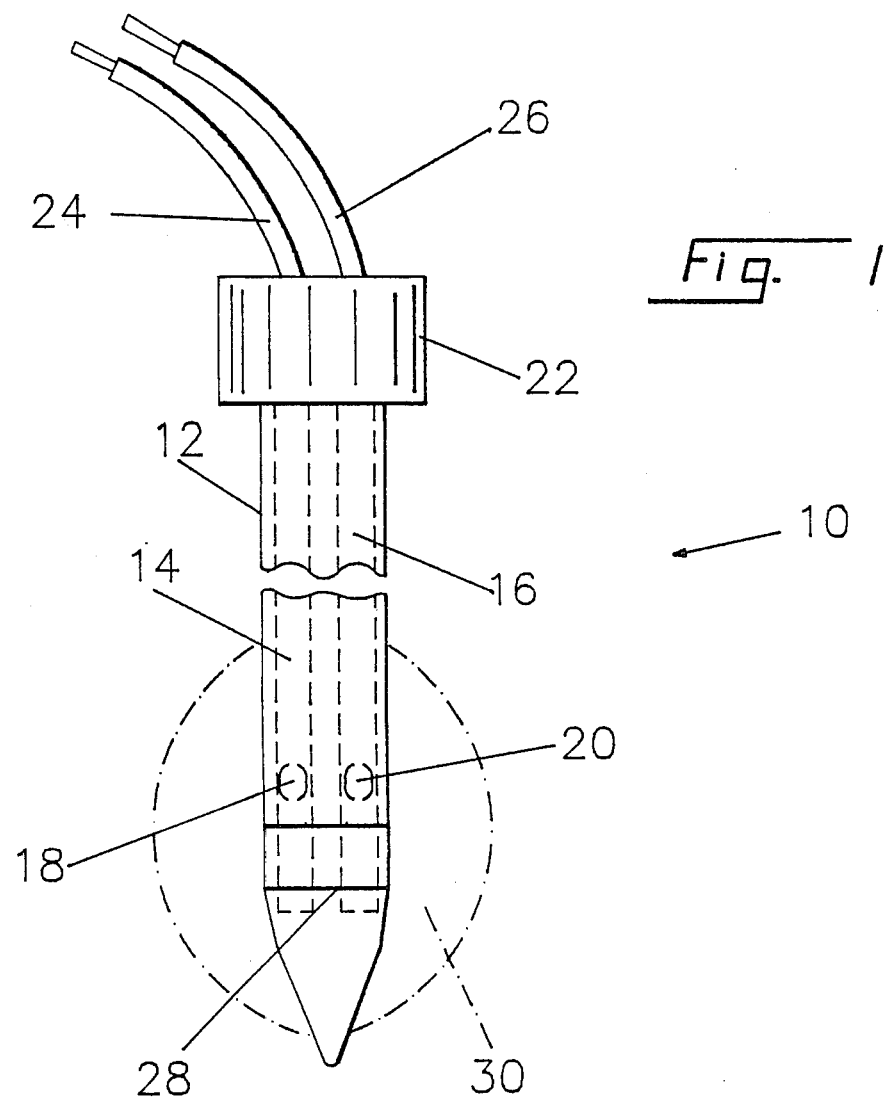
FIG. 1 is a side view of a catheter for microwave thermotherapy, including a shielded thermistor according to an embodiment of the invention.

Referring to FIG. 1, there is shown, generally at 10, a microwave thermotherapy catheter comprising one possible environment within which the apparatus of the present environment may be disposed. A catheter tube 12, preferably of a suitable semi-rigid material such as, for example, silicone rubber, includes first and second longitudinal openings or lumens 14 and 16, sealed at their lower ends. A microwave antenna 18 is disposed at a predetermined location within lumen 14. A thermistor 20 is disposed in lumen 16 close to the longitudinal position of microwave antenna 18. A sealing collar 22 at an upper end of catheter tube 12 permits the passage of a coaxial cable 24 from microwave antenna 18 and of conductors 26 from thermistor 20 for connection to external devices which are not of concern to the present invention. A plurality of radiopaque marker bands 28 on an exterior of catheter tube 12 are visible on an X-ray image to aid in the precise positioning of microwave thermotherapy catheter 10 in the tissue to be treated.

When microwave antenna 18 is energized from a suitable source of microwave energy (not shown), the temperature of surrounding tissue is increased. Typically, a football-shaped volume 30, generally centered on microwave antenna 18, is heated to treatment temperature. Thermistor 20, being within football-shaped volume 30, measures a temperature within lumen 16 which can be related to the temperature of adjacent areas outside catheter tube 12.

As noted in the description of the background of the invention, the close proximity of thermistor 20 and conductors 26 to microwave antenna 18 produces undesired microwave heating of thermistor 20 and a consequent error in the measured temperature. It is the purpose of the present invention to overcome this problem.

Referring now to FIG. 2, there is shown, generally at 32, a thermistor system according to an embodiment of the invention, and removed from catheter tube 12 (FIG. 1) for purposes of clarity of illustration and description. It has been discovered that a continuous, highly-conductive metallic coating on thermistor 20 and conductors 26 provides sufficient shielding against the heating effects of microwave radiation so that the undesired heating effects of the prior art are not experienced. One of the particular problems to be overcome includes providing a satisfactory interface for a conductive coating on thermistor 20 and on conductors 26. Conventional thermistors 20 include an outer coating of a varnish. Varnish is not amenable to being coated with a metallic coating. A further problem is producing a conductive coating on the surface of the flexible insulation on conductors 26. Such insulation is typically of a material such as, for example, fluorocarbon, which rejects coatings.

Referring now also to FIG. 3, in which some radial dimensions are grossly enlarged for illustration, a conventional thermistor bead 34, not shown in detail, is encased in a varnish coating 36. An aluminum foil layer 38 is wrapped upon varnish coating 36 with an overlapping portion 40 wrapped tightly over conductors 26 near thermistor 20. An electroplated layer 42, of a suitable high-conductance metal, is plated onto the surface of aluminum foil layer 38. One suitable material for electroplated layer 42 is gold.

Referring now to FIG. 4, conductor 26 is preferably of a bi-filar type wherein first and second electrical conductors 44 and 46 are integrally molded within a single plastic sheath 48, whereby electrical conductors 44 and 46 are held together in an assembly having constant spacing therebetween. An interface metallic layer 50 covers the entire surface of plastic sheath 48. A surface metallic layer 52 covers interface metallic layer 50.

The difficulty of forming interface metallic layer 50 on the surface of plastic sheath 48 may be solved in a suitable manner. One possibility includes electroless plating of a conducting material such as, for example, copper, onto plastic sheath 48. In the preferred embodiment, it has been found that a sputtering process is effective for producing an adhering continuous metallic layer on plastic sheath 48. The metal used for interface metallic layer 50 is preferably copper, but other suitable metals should not be considered outside the spirit and scope of the invention.

Surface metallic layer 52 may also be of any convenient material having low resistivity and suitability for the environment. Gold has been found to be nearly ideal. Surface metallic layer 52 is preferably coated onto interface metallic layer 50 by electroplating.

Referring again to FIGS. 2 and 3, prior to applying aluminum foil layer 38, varnish coating 36 covers and insulates not only thermistor bead 34, but also extends a substantial distance out upon plastic sheath 48 of conductor 26, whereby a continuous insulation is provided, including insulation at the interface between thermistor bead 34 and electrical conductors 44 and 46. Interface metallic layer 50 (FIG. 4) is first coated onto conductor 26 up to the junction with varnish coating 36. Aluminum foil layer 38 is then wrapped as tightly as possible onto thermistor 20 with overlapping portion 40 extending over a portion of conductor 26 that includes interface metallic layer 50. A dead soft type of foil is employed for aluminum foil layer 38 in order to permit it to conform to the shape of the elements on which it is wrapped. After wrapping aluminum foil layer 38, some electrical connection exists between aluminum foil layer 38 and interface metallic layer 50 due to the mechanical contact therebetween. Finally, the entire assembly is electroplated with gold, or other metal, to form electroplated layer 42 and surface metallic layer 52 in a single step. It has been found that the electroplating step further joins electroplated layer 42 and surface metallic layer 52 into a substantially continuous layer, thus providing a complete shield covering thermistor system 32.

In operation, electroplated layer 42 and surface metallic layer 52 preferably are grounded, whereby microwave energy is prevented from propagating inside. The length of interface metallic layer 50 and surface metallic layer 52, extending away from thermistor 20 is preferably great enough that microwave heating of an uncoated portion must pass such a long conduction path that negligible heat reaches thermistor 20. Thus, the temperature of thermistor 20 is independent of direct microwave heating and is, instead, responsive only to the temperature of the tissue being treated. This permits simultaneous temperature measurement and microwave irradiation without microwave-induced temperature-measurement errors.

Having described preferred embodiments of the invention with reference to the accompanying drawings, it is to be understood that the invention is not limited to those precise embodiments, and that various changes and modifications may be effected therein by one skilled in the art without departing from the scope or spirit of the invention as defined in the appended claims.

What is claimed is:

1. A thermistor assembly comprising:
    a thermistor;
    said thermistor including a first insulating coating thereon;
    electrical conductors connected to said thermistor;
    a second insulating coating on said electrical conductors;
    said first and second insulating coating forming a continuous insulation;
    an interface metallic layer on said second insulating coating;
    an electrically conductive foil wrapped upon said thermistor and in overlapping electrical contact with a portion of said interface metallic layer; and
    a surface metallic layer on said interface metallic layer and said electrically conductive foil.

2. A thermistor assembly according to claim 1 wherein said first insulating coating is a varnish.

3. A thermistor assembly according to claim 1 wherein said electrically conductive foil is an aluminum foil.

4. A thermistor assembly according to claim 1 wherein said surface metallic layer is gold.

5. A thermistor assembly according to claim 1 wherein said interface metallic layer is copper, sputtered in place upon said second insulating coating.

6. A thermistor assembly comprising:
    a thermistor;
    said thermistor including a varnish coating thereon;
    electrical conductors connected to said thermistor;
    a plastic layer on said electrical conductors;
    said varnish coating and said plastic layer forming a continuous insulation;
    an interface metallic layer of copper on said plastic layer;
    an aluminum foil wrapped upon said thermistor and in overlapping electrical contact with a portion of said interface metallic layer; and
    a surface metallic layer of gold electrically plated on said interface metallic layer and said aluminum foil.

7. A method for forming a shielding layer on a thermistor assembly comprising:
    forming a first insulating coating on a thermistor;
    forming a second insulating coating on electrical conductors connected to said thermistor;
    said first and second insulating coating forming a continuous insulation;
    sputtering an interface metallic layer on said second insulating coating;
    wrapping an electrically conductive foil upon said thermistor and in overlapping electrical contact with a portion of said interface metallic layer; and
    electroplating a surface metallic layer on said interface metallic layer and said electrically conductive foil.

* * * * *